US008987502B2

United States Patent
Rong et al.

(10) Patent No.: US 8,987,502 B2
(45) Date of Patent: Mar. 24, 2015

(54) OLEANOLIC ACID AMIDATE DERIVATIVES, PREPARATION METHODS AND USES THEREOF

(71) Applicant: Hangzhou Bensheng Pharmaceutical Co., Ltd., Zhejiang (CN)

(72) Inventors: Frank Rong, Zhejiang (CN); Rongzhen Xu, Zhejiang (CN); Fuwen Xie, Fujian (CN); Hongxi Lai, Fujian (CN)

(73) Assignee: Hangzhou Bensheng Pharmaceutical Co., Ltd., Zheijiang (CN)

( * ) Notice: Subject to any disclaimer, the term of this patent is extended or adjusted under 35 U.S.C. 154(b) by 0 days.

(21) Appl. No.: 14/361,991

(22) PCT Filed: Nov. 30, 2012

(86) PCT No.: PCT/CN2012/085671
§ 371 (c)(1),
(2) Date: May 30, 2014

(87) PCT Pub. No.: WO2013/079024
PCT Pub. Date: Jun. 6, 2013

(65) Prior Publication Data
US 2014/0343108 A1        Nov. 20, 2014

(30) Foreign Application Priority Data

Dec. 1, 2011    (WO)   ................. PCT/CN2011/083295

(51) Int. Cl.
| | | |
|---|---|---|
| C07C 69/74 | (2006.01) |
| C07D 333/38 | (2006.01) |
| C07D 213/82 | (2006.01) |
| C07C 233/60 | (2006.01) |
| C07C 231/02 | (2006.01) |
| C07D 307/68 | (2006.01) |
| C07D 307/54 | (2006.01) |
| C07C 233/74 | (2006.01) |
| C07C 235/54 | (2006.01) |

(52) U.S. Cl.
CPC ............. *C07D 333/38* (2013.01); *C07D 213/82* (2013.01); *C07C 233/60* (2013.01); *C07C 231/02* (2013.01); *C07D 307/68* (2013.01); *C07D 307/54* (2013.01); *C07C 233/74* (2013.01); *C07C 235/54* (2013.01)
USPC ....................................................... 560/116

(58) Field of Classification Search
CPC ......................................................... C07J 63/00
USPC ......................................................... 560/116
See application file for complete search history.

(56) References Cited

FOREIGN PATENT DOCUMENTS

| CN | 101367861 A | 2/2009 |
|---|---|---|
| CN | 102083442 A | 6/2011 |
| WO | 2013079024 A1 | 6/2013 |

OTHER PUBLICATIONS

Meng et al. 'Synthesis and anti-tumor activity of oleanolic acid derivatives'. Acta pharmaceutica Sinica. 2011, vol. 46, No. 10, pp. 1215-1220.
International Search Report for International Application No. PCT/CN2012/085671, dated Feb. 14, 2013 (4 pages).
Written Opinion of the International Searching Authority for International Application No. PCT/CN2012/085671 dated Feb. 14, 2013 (8 pages).

*Primary Examiner* — Nizal Chandrakumar
(74) *Attorney, Agent, or Firm* — Lathrop & Gage LLP; Brian C. Trinque

(57) ABSTRACT

The present invention belongs to the field of natural medicine and pharmaceutical chemistry, and specifically relates to novel amidated derivatives of oleanolic acid according to formula (I) or a pharmaceutically acceptable salt thereof, to a process for the preparation of these compounds, compositions containing such compounds and their use in preparing antineoplastic medicaments.

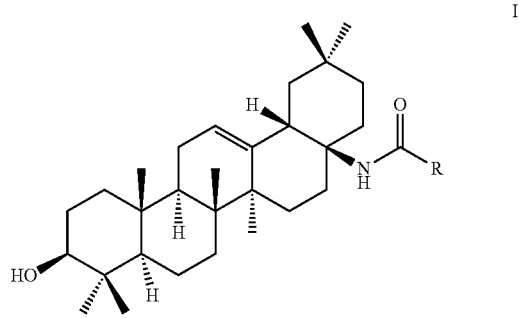

11 Claims, No Drawings

OLEANOLIC ACID AMIDATE DERIVATIVES, PREPARATION METHODS AND USES THEREOF

RELATED APPLICATIONS

This application is a 35 U.S.C. §371 filing of International Application No. PCT/CN2012/085671, filed Nov. 30, 2012, which claims priority to International Application No. PCT/CN2011/083295, filed Dec. 1, 2011, each of which is incorporated herein by reference in its entirety.

TECHNICAL FIELD

The present invention belongs to the field of natural medicine and pharmaceutical chemistry, and relates to novel oleanolic acid derivatives, in particular oleanolic acid derivatives amidated at C-17 position, to a process for the preparation of these compounds, compositions containing such compounds and their use in preparing antineoplastic medicaments.

BACKGROUND OF THE INVENTION

Oleanolic acid (OA), also known as caryophyllin, is a type of pentacyclic triterpenoids. It is extracted from the leaves and fruits of Oleaceae, Gentianaceae, Rubiaceae, Amaranthaceae, and the like, and is mainly present in free form and (or) in combination with saccharides. Many scientists, domestic and overseas, have conducted extensive research on pentacyclic triterpenoids. According to the literature, oleanolic acid and derivatives or analogs thereof exhibit a variety of biological activities, such as anti-inflammation, antitumor, antivirus, immunoregulation, inhibition of platelet aggregation, hypolipidemic, liver protection, kidney protection, anti-HIV, etc. (LI, Yingxia et al., An oleanolic acid-lactose conjugate, the preparation process and use thereof, [P] CN 1414012 A. 2003; ZHANG, Yihua et al., An oleanolic acid derivative, the preparation process and use thereof, [P] CN 102070697 A. 2011; Lin, Z. H.; Zhang, Y.; Zhang, Y. N.; Shen, H.; Hu, L. H.; Jiang, H. L.; Shen, X. Oleanolic acid derivative NPLG441 potently stimulates glucose transport in 3T3-L1 adipocytes via a multi-target mechanism. Biochemical Pharmacology. 2008. 76:1251-1262; Chen, J.; Gong, Y. C.; Liu, J.; Hua, W. Y.; Zhang, L. Y.; Sun, H. B. Synthesis and biological evaluation of novel pyrazolo[4,3-b]oleanane derivatives as inhibitors of glycogen phosphorylase. Chemistry & Biodiversity. 2008. 5: 1304-1312).

Oleanolic acid, the derivatives and analogs thereof

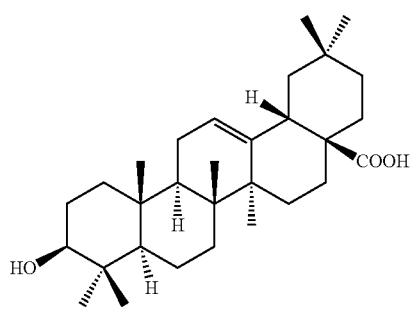

Oleanolic acid

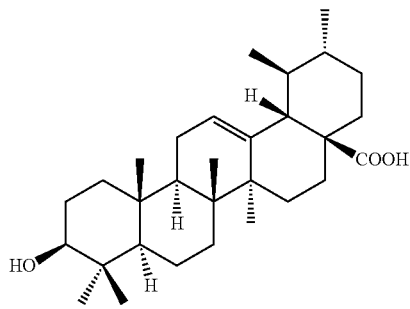

Ursolic acid

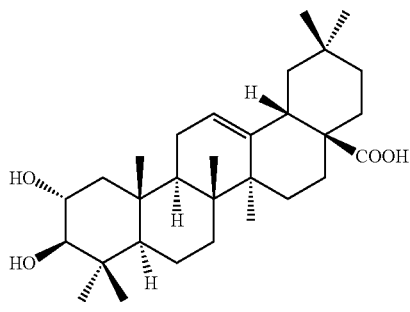

Maslinic acid

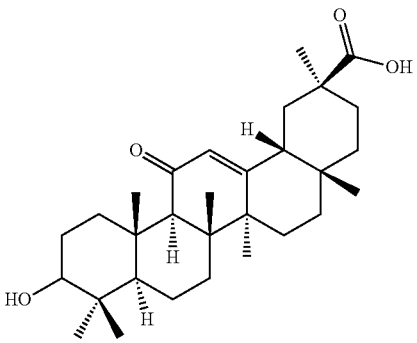

Glycyrrhetinic acid

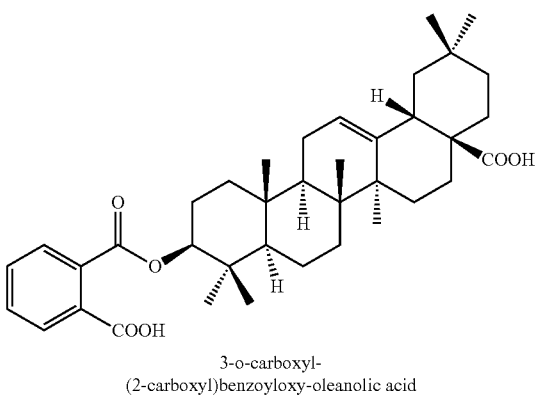

3-o-carboxyl-(2-carboxyl)benzoyloxy-oleanolic acid

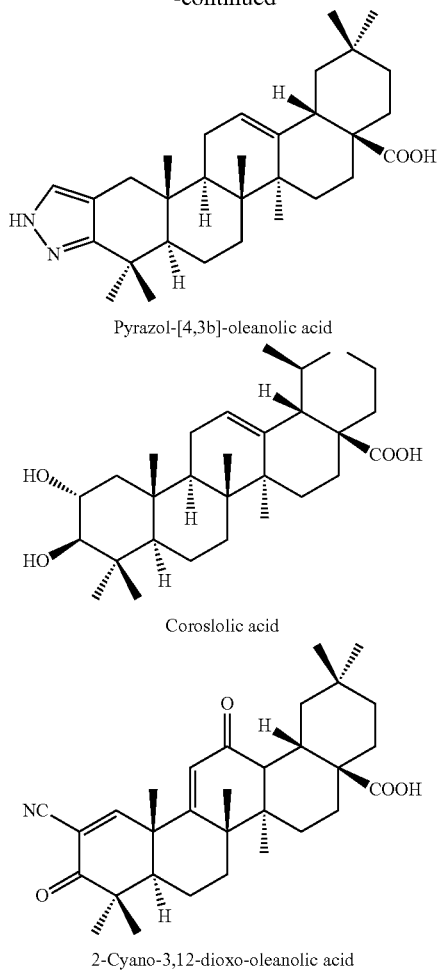

Pyrazol-[4,3b]-oleanolic acid

Coroslolic acid

2-Cyano-3,12-dioxo-oleanolic acid

Nowadays, malignant tumor is the most serious common disease and poses threats to human health. The development of anti-tumor drugs is an important research topic of modern medicine. It has become a focus of the anti-tumor research domestic and overseas to search for drugs with high efficacy and low toxicity from Chinese herbal plants. Oleanolic acid, with low toxicity and having abundant resource in Chinese herbal medicine, is a very promising anti-tumor drug.

Recent years witnessed the literature report of oleanolic acid for its function against human lung cancer cell proliferation, and its ability of anti-invasion and inducing cell apoptosis. Researchers observed the effects of oleanolic acid on the invasion ability of PGCL3 cells through cell proliferation inhibition assay, soft agar colony formation assay, and the like. Results showed that oleanolic acid could reduce proliferation of PGCL3 cells in a dose-dependent correlation, had the effects of anti-proliferation and anti-invasion of PGCL3 human lung cancer cells, and had the effect of inducing apoptosis of PGCL3 cells. Its anti-invasion effect lies not only in the blocking of a particular step of the invasion, but the inhibition of each basic step of the invasion. In addition, researchers explored the effect of oleanolic acid on A549 cells and the possible mechanism thereof, and the results showed that oleanolic acid was capable of a concentration-dependent induction of apoptosis of human lung adenocarcinoma cells. (ZHANG Dongfang et al., Study on proliferation inhibition and anti-invasion and apoptotic induction of oleanolic acid in human lung cancer cell line, 2003, 30 (3): 081-381; WEI Xiaohong et al., Apoptosis induced by oleanolic acid and its relation to intracellular calcium of human lung adenoma A549 cells, Journal of Tongji University (Medical Science), 2009, 30 (5): 19-23.)

Literature reported that researchers studied the inhibition of ovarian cancer cell line IGROV1 and human breast cancer cell line MDA-MB-231 by oleanolic acid via detecting the activity of tumor cells through inhibition tests of cell proliferation and MTT method. The results showed that oleanolic acid could reduce the proliferation ability of IGROV1 and MDA-MB-231 cells in a dose-dependent correlation, which indicated that oleanolic acid had inhibitory activity against these two malignant tumor cell lines. (WU, Linwei et al., Inhibiting Effect of Oleanolic Acid on Ovarian Carcinomas IGROV1 and Breast Cancer Cell Line MDA-MB-231, Chinese Journal of Applied and Environmental Biology, 2010, 16(2): 202-204.)

Recently, LIN Xiukun et al. reported the excellent anti-pancreatic cancer effects of oleanolic acid and pharmaceutical preparations thereof, which was represented by the obvious inhibitory activity on human pancreatic cancer cells in vitro and the significant antitumor activity on nude mice with transplanted tumor of these tumor cells. In addition, LIN Xiukun et al. also studied the inhibitory effect of oleanolic acid on cervical cancer. The results showed that oleanolic acid and pharmaceutical preparations thereof had obvious in vitro inhibitory activity on human cervical carcinoma cells and also had significant antitumor activity on transplanted tumor in nude mice of these tumor cells. (LIN Xiukun et al., Anti-pancreatic carcinoma effects of oleanolic acid and pharmaceutical preparations thereof, [P] CN 102151275 A. 2011; LIN Xiukun et al., Anti-cervical cancer effects of oleanolic acid and pharmaceutical preparations thereof, [P] CN 102133219 A. 2011.)

Oleanolic acid is widely applied in clinics due to its various pharmacological activities and low toxicity, but this type of drug has low bioavailability in a human body. Therefore, oleanolic acid derivatives with high efficiency and low toxicity have good prospects in industry. The present invention modified oleanolic acid on its C-17 position by amino substitution and introduced functional groups to improve its biological activity and bioavailability. Up to now, report on the method of the present invention and the amidated derivatives of oleanolic acid by amino-substitution on C-17 position have not yet been seen in the literature.

SUMMARY OF THE INVENTION

One object of the present invention is to provide novel amidated oleanolic acid derivatives of formula (I)

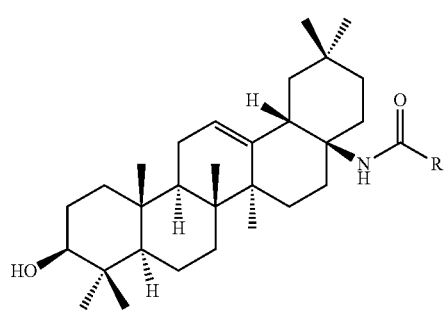

I wherein R is selected from the group consisting of H, optionally substituted $C_3$-$C_7$ cycloalkyl or cycloalkenyl, optionally substituted aryl, optionally substituted heterocyclyl or heteroaryl, optionally substituted aryl-vinyl, and optionally substituted heteroaryl-vinyl, each of which is optionally substituted with a substituent selected from the group consisting of halogen, nitro, cyano, amino, hydroxyl, thiol, carboxyl, $C_1$-$C_6$ alkyl, $C_1$-$C_6$ alkylamino, $C_1$-$C_6$ alkoxy, and $C_1$-$C_6$ alkylthio;

or a pharmaceutically acceptable salt thereof.

The second object of the present invention is to provide a process for preparing the amidated oleanolic acid derivatives of formula (I) of the present invention,

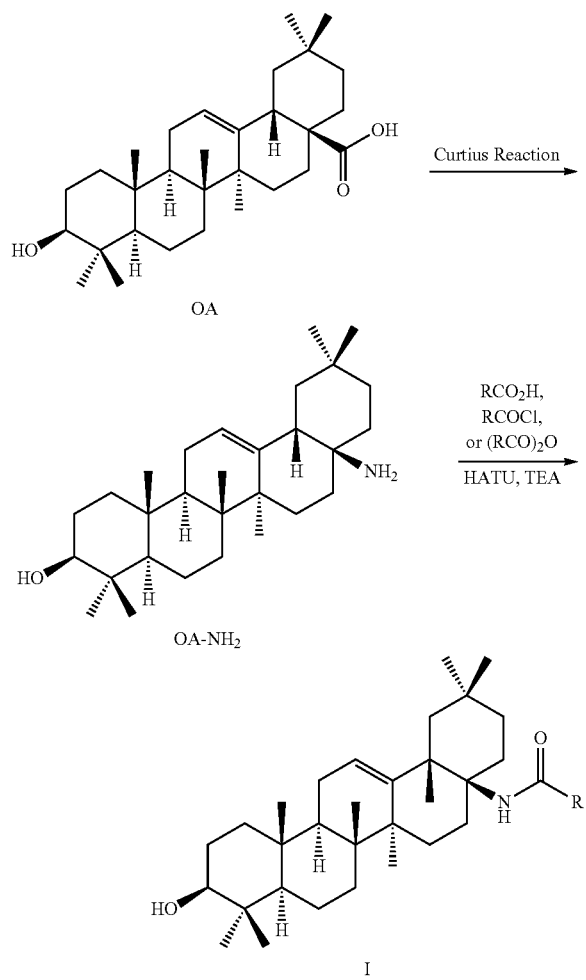

comprising first subjecting oleanolic acid to Curtius Reaction to produce an aminated oleanolic acid intermediate (OA-NH$_2$), and then subjecting the intermediate to an amide bond formation reaction with an organic acid, an organic acyl chloride or an organic anhydride to produce the amidated oleanolic acid derivative of formula (I), wherein R in formula (I) is as defined in the formula (I) above.

The third object of the present invention is to provide a pharmaceutical composition comprising the compound of the present invention, said pharmaceutical composition comprising at least one compound of the present invention and optionally a pharmaceutically acceptable excipient.

The fourth object of the present invention is to provide the use of the compound of the present invention or the pharmaceutical composition comprising the same in the manufacture of a medicament, in particular an antitumor medicament. Correspondingly, the present invention provides a method for treating a subject suffering from tumor, comprising administrating to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor, prostate cancer, and the like.

The present invention also relates to the compounds of the present invention used for treating a tumor.

SPECIFIC EMBODIMENTS OF THE INVENTION

The present invention relates to a novel amidated oleanolic acid derivative of formula (I),

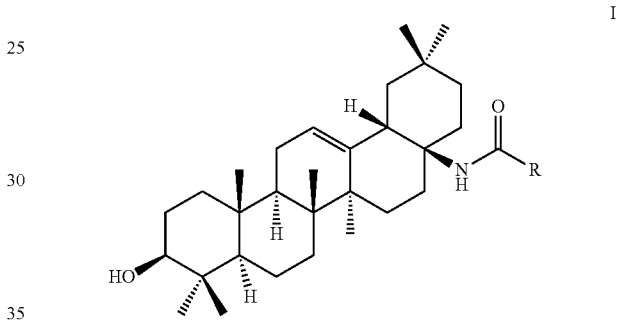

wherein R is selected from the group consisting of H, optionally substituted $C_3$-$C_7$ cycloalkyl or cycloalkenyl, optionally substituted aryl, optionally substituted heterocyclyls or heteroaryl, optionally substituted aryl-vinyl, and optionally substituted heteroaryl-vinyl, each of which is optionally substituted with a substituent selected from the group consisting of halogen, nitro, cyano, amino, hydroxyl, thiol, carboxyl, $C_1$-$C_6$ alkyl, $C_1$-$C_6$ alkylamino, $C_1$-$C_6$ alkoxy, and $C_1$-$C_6$ alkylthio;

or a pharmaceutically acceptable salt thereof.

According to a preferred embodiment of the present invention, R is selected from the group consisting of aryl, heteroaryl, cycloalkyl, heterocyclyl, aryl-vinyl, and heteroaryl-vinyl, each of which is optionally substituted with halogen, $C_1$-$C_6$ alkyl or $C_1$-$C_6$ alkoxy.

According to another preferred embodiment of the present invention, the aryl is phenyl.

According to a preferred embodiment of the present invention, the heteroaryl is selected from the group consisting of furyl, thienyl, pyrrolyl, and pyridyl.

According to a preferred embodiment of the present invention, the cycloalkyl is selected from the group consisting of cyclopropyl, cyclopentyl and cyclohexyl.

According to a preferred embodiment of the present invention, the heterocyclic radical is selected from the group consisting of tetrahydrofurayl, tetrahydrothienyl, piperidyl, piperazinyl and morpholinyl.

According to a preferred embodiment of the present invention, R is selected from the group consisting of optionally substituted heteroaryl-vinyl.

Part of the preferred amidated oleanolic acid derivatives according to the present invention is shown as below. These examples are only for further illustrating the present invention, without any restriction to the scope of the present invention.
BS-OA-096
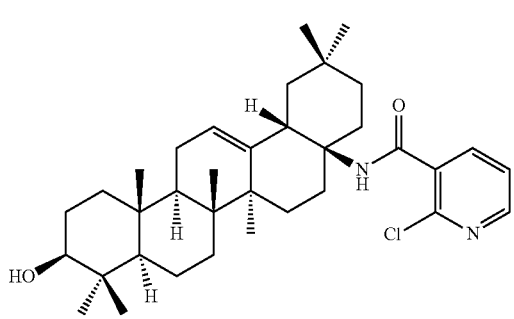
BS-OA-097
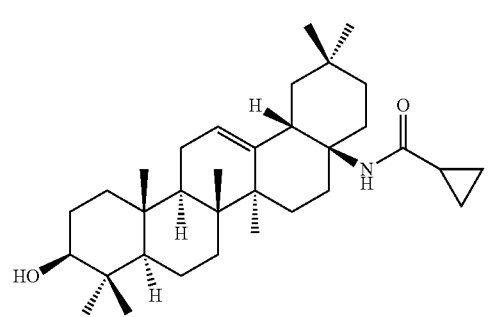
BS-OA-098
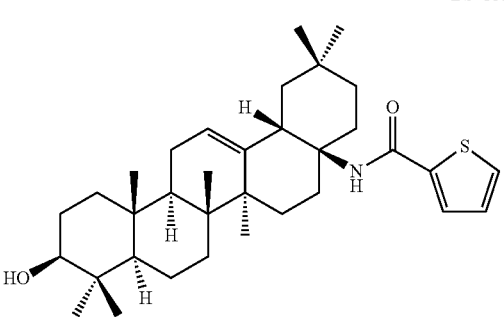
BS-OA-099
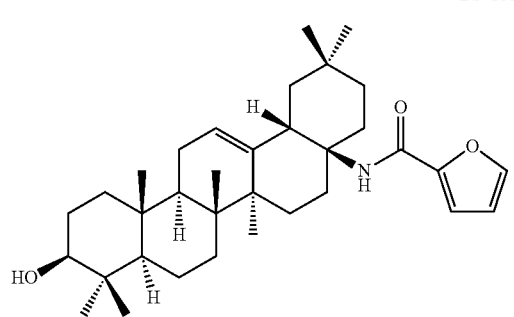
-continued
BS-OA-100
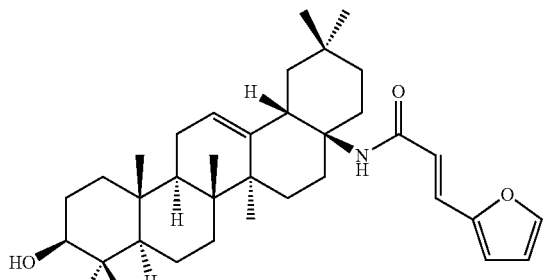
BS-OA-101
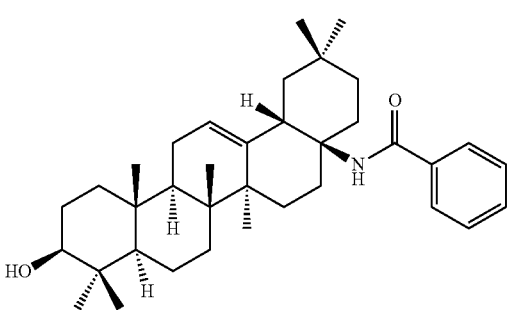
BS-OA-102
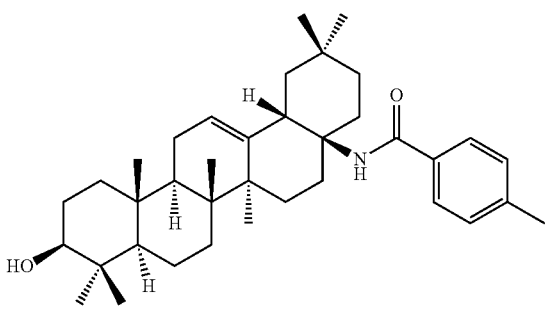
BS-OA-103
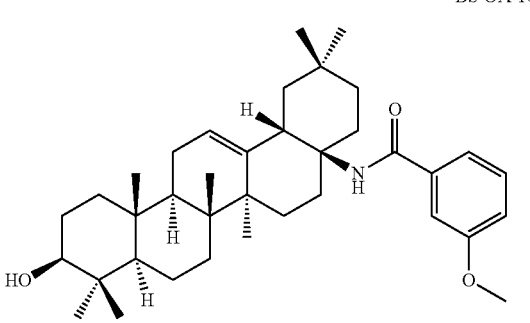
BS-OA-104
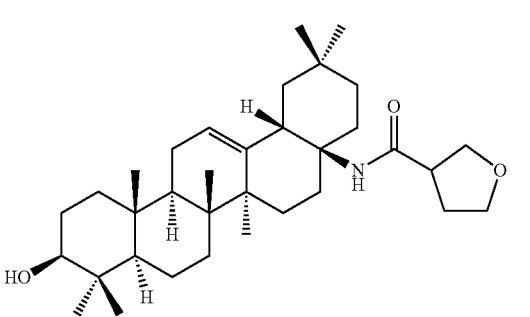

Some data for the above compounds is listed in the table below:

| Compound No. | Formula | Molecular Weight | Appearance | State | Total Yield (%) |
|---|---|---|---|---|---|
| BS-OA-096 | $C_{35}H_{51}ClN_2O_2$ | 567.2 | White | Solid | 1.4 |
| BS-OA-097 | $C_{33}H_{53}NO_2$ | 495.8 | White | Solid | 4.4 |
| BS-OA-098 | $C_{34}H_{51}NO_2S$ | 537.8 | White | Solid | 3.5 |
| BS-OA-099 | $C_{34}H_{51}NO_3$ | 521.8 | White | Powder | 9.5 |
| BS-OA-100 | $C_{36}H_{53}NO_3$ | 547.8 | White | Solid | 4.7 |
| BS-OA-101 | $C_{36}H_{53}NO_2$ | 531.8 | White | Powder | 8.9 |
| BS-OA-102 | $C_{37}H_{55}NO_2$ | 545.8 | White | Powder | 12.3 |
| BS-OA-103 | $C_{37}H_{55}NO_3$ | 561.8 | White | Solid | 5.2 |
| BS-OA-104 | $C_{34}H_{55}NO_3$ | 525.8 | White | Solid | 4.5 |

In another embodiment of the present invention, the following compounds of formula (I) are particularly preferred:

BS-OA-096

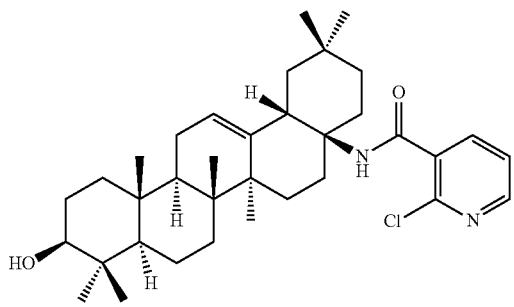

17-(2-chloropyridinylcarboxamide) oleanolic acid

BS-OA-097

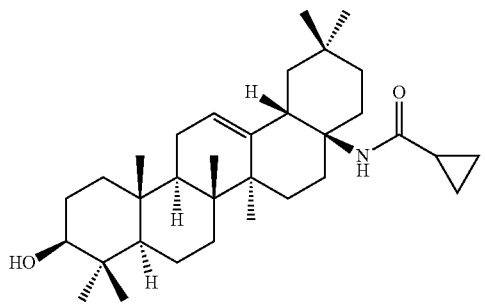

17-cyclopropanycarboxamide oleanolic acid

BS-OA-099

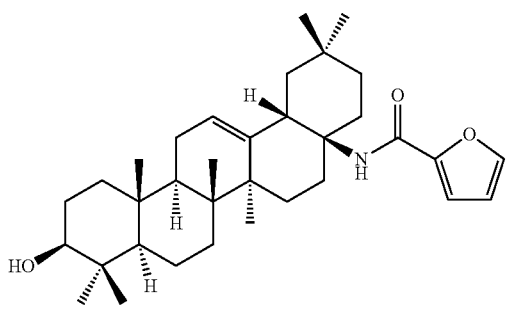

17-(furan-2-ylcarboxamide) oleanolic acid

BS-OA-103

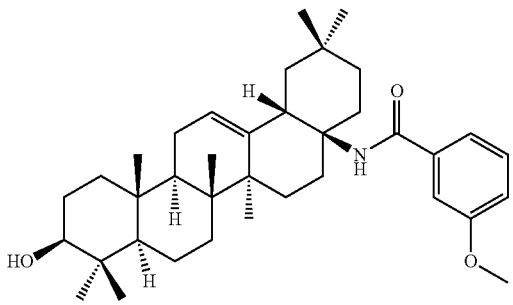

17-(3-methoxybenzamide) oleanolic acid

The amidated oleanolic acid derivatives of the present invention have an antitumor activity. As compared with oleanolic acid per se, the amidated oleanolic acid derivatives of the present invention have an improved antitumor activity, for example by several folds or even tens of folds.

As used herein, the term "alkyl" refers to a straight or branched hydrocarbon radical containing designated number of carbon atoms derived from alkanes. The alkyl can comprise 1-18 carbon atoms, such as 1-12, 1-10, 1-8, 1-6, 1-5, 1-4 or 1-3 carbon atoms. Examples of the alkyl include, but not limited to, methyl, ethyl, n-propyl, isopropyl, tert-butyl, n-pentyl, n-hexyl and n-octadecyl.

The term "$C_3$-$C_7$ cycloalkyl or cycloalkenyl" refers to a saturated or unsaturated 3-7 membered monocyclic hydrocarbon radical. Representative examples of $C_3$-$C_7$ cycloalkyl or cycloalkenyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 carbon atoms (such as 6-12 or 6-10 carbon atoms). In the case of polycyclic aryl, at least one ring is aromatic. Aryl can also be one fused with a heterocyclyl. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring member(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocyclic group, and the other ring(s) can be aromatic or non-aromatic, with or without a heteroatom. Examples of heteroaryl include such as pyrrolyl, pyrazolyl, imidazolyl, oxazolyl, pyridinyl, pyrimidinyl, furanyl, thiophenyl, isoxazolyl, indolyl, etc.

The term "heterocyclyl" refers to a non-aromatic cyclic group containing 1-4 heteroatoms (e.g. 1, 2, 3 or 4 heteroatoms) as ring member(s). A heteroatom refers to nitrogen, oxygen or sulfur. A heterocyclyl can be a monocyclic heterocyclyl having 4-8 ring atoms (such as 4-7 membered ring, 5-7 membered ring or 5-6 membered ring) or a bicyclic heterocyclyl having 7-11 ring atoms. A heterocyclic radical can be aromatic or non-aromatic. Examples of heterocyclyl include azacyclobutyl, pyrrolidinyl, pyrrolinyl, tetrahydrofuranyl, dihydrofuranyl, piperazinyl, piperidinyl, morpholinyl, thiomorpholinyl, tetrahydropyranyl, tetrahydrothiophenyl, etc.

The term "aryl-vinyl" refers to a vinyl group substituted by the above aryl.

The term "heteroaryl-vinyl" refers to a vinyl group substituted by the above heteroaryl.

The term "halogen" refers to fluorine, chlorine, bromine or iodine.

The term "alkylamino" refers to an amino group substituted with one or two alkyl having designated number of carbon atoms.

The term "alkoxy" refers to alkyl-O— radical, wherein the alkyl is defined as above.

The term "alkylthio" refers to alkyl-S— radical, wherein the alkyl is defined as above.

As used herein, the term "pharmaceutically acceptable salts of the compounds of formula (I)" can be exemplified as organic acid salts formed by an organic acid which comprises a pharmaceutically acceptable anion. These organic acid salts include, but not limited to, tosylate, methanesulfonate, malate, acetate, citrate, malonate, tartrate, succinate, benzoate, ascorbate, α-ketoglutarate, lactate, and α-glycerophosphate. Suitable inorganic salts may also be formed, including but not limited to, hydrochloride, sulfate, nitrate, bicarbonate and carbonate, phosphate, hydrobromate, hydriodate and the like.

A pharmaceutically acceptable salt may be obtained using standard procedures well known in the art, for example by reacting a sufficient amount of alkaline compound with a suitable acid that provides a pharmaceutically acceptable anion.

The main structure of the amidated oleanolic acid derivatives of the present invention has eight chiral centers in the stereochemical structure represented by the structural formula (I). The stereochemical definitions and conventions used herein generally follow MCGRAW-HILL DICTIONARY OF CHEMICAL TERMS (S. P. Parker, Ed., McGraw-Hill Book Company, New York, 1984); and ELIEL, E. AND WILEN, S., STEREOCHEMISTRY OF ORGANIC COMPOUNDS (John Wiley & Sons, Inc., New York, 1994). Many organic compounds are present in optically active forms, i.e., they have the ability to rotate plane-polarized light.

The terms "treatment," "treating," "treat," and the like used herein refer generally to obtaining a desired pharmacological and/or physiological effect. The effect may be prophylactic in terms of completely or partially preventing a disease or symptoms thereof, and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the compound of formula (I) of the present invention is prepared as follows.

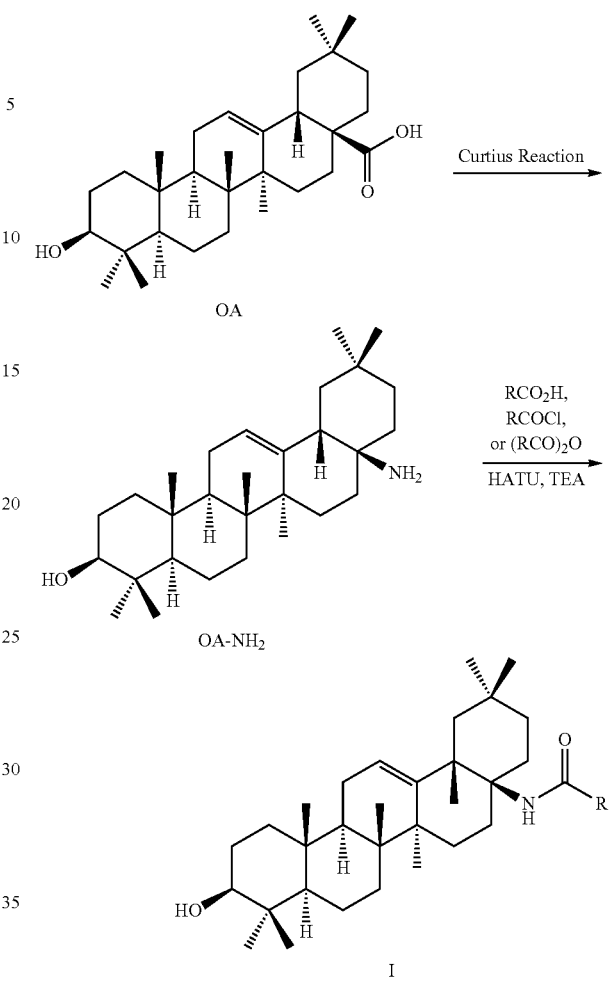

The amidated oleanolic acid derivative of formula (I) can be prepared by subjecting oleanolic acid extracted from natural herbal medicines to Curtius Reaction to produce an oleanolic acid aminated intermediate ($OA-NH_2$), and then subjecting the intermediate to an amido bond formation reaction with an organic acid, an organic acyl chloride or an organic anhydride in the presence of a coupling agent to produce the amidated oleanolic acid derivative of formula (I), wherein R in formula (I) is as defined above for the formula (I).

The above Curtius Reaction for amination typically produces firstly an azide intermediate in the presence of an alkali or an alkaline agent. Such azide intermediate is then decomposed to produce an aminated oleanolic acid intermediate ($OA-NH_2$) under heating in the presence of an acid or an acidic agent.

The alkali used to produce the azide intermediate can be, but not limited to, an organic alkali, such as triethylamine.

The acid used to decompose the azide intermediate can be, but not limited to, an inorganic acid, such as sulfuric acid.

The azide agent used in the Curtius Reaction can be an organic agent or an inorganic agent, such as sodium azide and diphenyl azidophosphate.

The above azido-amination reaction typically occurs in a solvent. The solvent used includes, but not limited to, a polar solvent, such as chloroform.

The reaction temperature for the above amination reaction is typically 40° C. to 120° C., such as 100° C.

The organic acid, the organic acyl chloride and the organic anhydride for the above amidation are all commercially available.

The amidation reaction typically occurs in the presence of a condensing agent, wherein the condensing agent can be, but not limited to, an organic condensing agent, such as 2-(7-azobenzotriazol-1-yl)-N,N,N',N'-tetramethyluronium hexafluorophosphate (HATU), benzotriazol-1-yl-N,N,N',N'-tetramethyluronium hexafluoroborate (HBTU), (benzotriazol-1-yloxy)tris(dimethylamino)phosphonium hexafluorophosphate (BOP), benzotriazolyl-N,N,N',N'-tetramethyluronium hexafluoroborate (TBTU).

The amidation reaction is typically carried out in the presence of an alkali. The alkali herein can be, but not limited to, an organic alkali, such as N,N-diisopropylethylamine (DIPEA), triethylamine (TEA), pyridine or 4-dimethylaminopyridine (DMAP).

The amidation reaction is typically carried out in a solvent and it may also be carried out in the absence of a solvent. The solvent used herein includes, but not limited to, organic polar solvents, such as dichloromethane (DCM), tetrahydrofuran (THF), N,N-dimethylformamide (DMF) or dimethylsulfoxide (DMSO), etc.

The typical operation of the amidation reaction can be, but not limited to, as follows. An organic acid, an alkali and a condensing agent are added to N,N-dimethylformamide (DMF) in a suitable proportion. Stir the mixture for 30 minutes under normal temperature and then add a N,N-dimethylformamide (DMF) solution of the oleanolic acid intermediate (OA-NH$_2$). After the mixture is stirred under room temperature and allowed to react for 12 hours, an organic solvent is used to extract the product, which is then washed with water and saturated brine, followed by drying and concentration to give the crude product. The crude product is then purified with HPLC to give the pure product.

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from being interfered in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including mixing, dissolving, or freeze drying processes.

The compounds of the present invention may be formulated into a pharmaceutical composition and administered to a subject in a route suitable for the selected administration manner, e.g., orally, by gastrointestinal perfusion, or by intravenous, intramuscular or subcutaneous injection.

Thus, the present compounds may be systemically administered, e.g., orally administered, in combination with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredients (optionally encapsulated in liposomes), which are adapted for an extemporaneous preparation of sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceride, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The amidated oleanolic acid derivative of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be prepared by a synthesis method known in the art.

Example 1

Synthesis of compound BS-OA-102

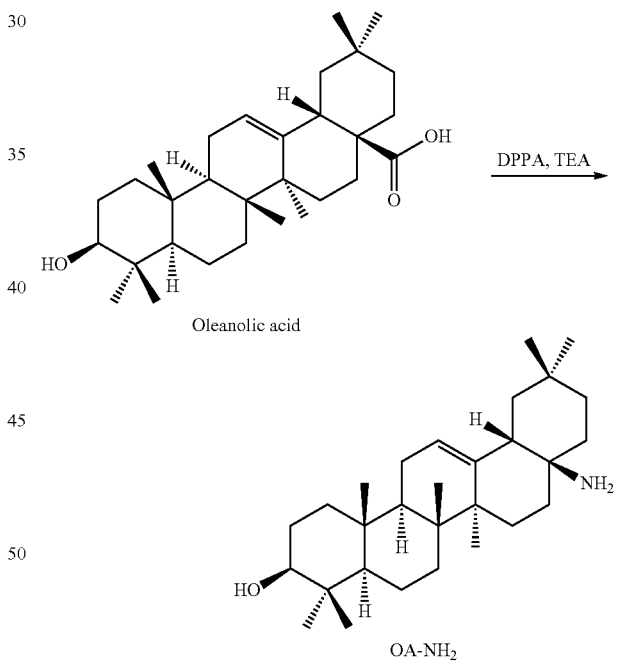

wherein, DPPA: diphenyl phosphoryl azide: TEA: triethylamine.

Oleanolic acid (2.5 g, 5.5 mmol) is dissolved in chloroform (25 mL), to which diphenyl phosphoryl azide (1.8 g, 6.6 mmol) and triethylamine (0.66 g, 6.6 mmol) are added. The reaction solution is stirred for 12 h under room temperature and then 3M sulfuric acid (15 mL) is added thereto. The reaction solution is heated to 100° C. and the stirring continues for 6 hours. After the reaction is completed, the reaction solution is cooled to room temperature, adjusted with NaOH (aq. 10%) to pH 13, and then extracted with ethyl acetate (40 mL*2). The organic phase is combined, dried and concentrated to give compound OA-NH₂ as a yellow oil, which is directly used in the subsequent reaction without purification.

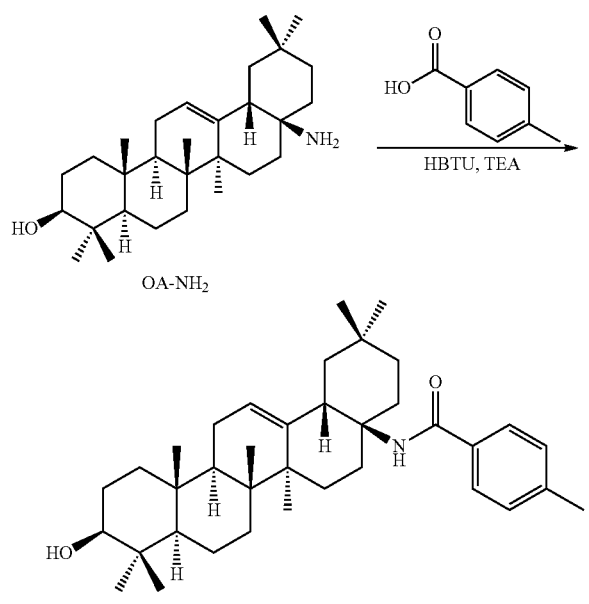

wherein, HBTU: benzotriazolyl-N,N,N',N'-tetramethyluronium hexafluorophosphate.

To N,N-dimethylformamide (0.5 mL) are added p-toluic acid (15.1 mg, 0.1 mmol), benzotriazolyl-N,N,N',N'-tetramethyluronium hexafluorophosphate (45.5 mg, 0.12 mmol) and triethylamine (30.3 mg, 0.30 mmol). After the reaction solution is stirred for 30 minutes under room temperature, OA-NH₂ (110 mg) is added and the reaction solution is stirred for 12 hours under room temperature. After the reaction is completed, the solution is extracted and concentrated. The resulted crude product is separated and purified via a preparative chromatographic column to give compound BS-OA-102 (16.1 mg, yield 12.3%) as a white solid.

LC-MS: retention time: 1.74 min (97.56%), m/z: 546.7 (M+H).

1H NMR (300 MHz, CDCl3) δ 7.60 (d, J=8.2 Hz, 1H), 7.33 (s, 1H), 7.19 (t, 2H), 5.86 (s, 1H), 5.40 (s, 1H), 3.20 (s, 1H), 2.62 (d, 1H), 2.37 (s, 2H), 2.31 (m, 2H), 2.00 (s, 2H), 1.94 (m, 3H), 1.69 (m, 2H), 1.62 (m, 4H), 1.56 (m, 2H), 1.50-1.22 (m, 10H), 1.17 (s, 3H), 0.92 (m, 9H), 0.84 (m, 2H), 0.74 (m, 5H).

BS-OA-096 is prepared according to the process for BS-OA-102 using the same reagents by reacting OA-NH₂ with 2-chloronicotinic acid. LC-MS: 1.37 min (97.92%), m/z: 568.6 (M+H).

BS-OA-097 is prepared according to the process for BS-OA-102 using the same reagents by reacting OA-NH₂ with cyclopropanecarboxylic acid. LC-MS: 1.40 min (86.38%), m/z: 496.5 (M+H), 518.5 (M+Na).

BS-OA-098 is prepared according to the process for BS-OA-102 using the same reagents by reacting OA-NH₂ with thiophene-2-carboxylic acid. LC-MS: 1.55 min (99.73%), m/z: 538.5 (M+H), 560.6 (M+Na).

BS-OA-099 is prepared according to the process for BS-OA-102 using the same reagents by reacting OA-NH₂ with furan-2-carboxylic acid. LC-MS: 1.55 min (98.47%), m/z: 522.5 (M+H).

BS-OA-100 is prepared according to the process for BS-OA-102 using the same reagents by reacting OA-NH₂ with 2-furanacrylic acid. LC-MS: 1.43 min (98.69%), m/z: 549.8 (M+H).

BS-OA-101 is prepared according to the process for BS-OA-102 using the same reagents by reacting OA-NH₂ with benzoic acid. LC-MS: 1.61 min (98.42%), m/z: 532.6 (M+H).

BS-OA-103 is prepared according to the process for BS-OA-102 using the same reagents by reacting OA-NH₂ with 3-methoxybenzoic acid. LC-MS: LC-MS: 1.58 min (98.59%), m/z: 562.6 (M+H).

BS-OA-104 is prepared according to the process for BS-OA-102 using the same reagents by reacting OA-NH₂ with tetrahydrofuran-2-carboxylic acid. LC-MS: 1.32 min (98.25%), m/z: 526.6 (M+H), 548.5 (M+Na).

Example 2

Evaluation of the Amidated Oleanolic Acid Derivatives of the Present Invention for their Anti-Leukemia Activities (1) Experimental Materials Leukemia cell lines: leukemia cell lines: K562/adr (drug-resistant, chronic myeloid leukemia, CML), NB4 (acute promyelocytic leukemia, AML), Kasumi-1 (acute myeloid leukemia M2 type, AML-M2), Jurkat (acute lymphoblastic leukemia, ALL), all of which are donated by Cancer Research Institute of Zhejiang University, China; and H9 (acute lymphoblastic leukemia, ALL), which is purchased from China Center for Type Culture Collection (CCTCC).

Reagents: The standard sample of oleanolic acid (OA) is purchased from Hua Kang Pharmaceutical Raw Material Factory, Shifang City, Sichuan, China; and the amidated oleanolic acid derivatives are prepared according to the present invention.

Main apparatuses: cell incubator (model: Thermo Scientific 3111) and a microplate absorbance reader (model: Bio-Rad iMark).

(2) Experimental Method

Obtaining 6000 well-growing leukemia cells and inoculating them into wells of a 96-well cell culture plate. The culture medium is the 1640 cell culture medium containing 10% fetal bovine serum. After adding the amidated oleanolic acid derivatives of different concentrations and mixing uniformly, placing the plate in a carbon dioxide cell incubator (5% $CO_2$) at 37° C. and incubated for 72 hours. Then the relative number of viable cells is determined by the MTT method. In this experiment, the cell proliferation inhibition rate in control group (not treated with any compound) is set as 0%. Based on the relative number of living cells, the half maximum inhibitory concentration for the leukemia cells at 72 hours ($IC_{50}$ value of 72 hours, μg/mL) and the inhibition rate (IR) of leukemia cell proliferation by the 16 μg/mL compound at 72 hours are calculated.

(3) Experimental Results

Experimental results are shown in table 1. Table 1 shows that the amidated oleanolic acid derivatives of the present invention can induce cell death of human chronic myeloid leukemia cells, acute myeloid leukemia cells and acute lymphocytic leukemia cells, and inhibit the growth of these leukemia cells. Specifically, the inventive amidated oleanolic acid derivatives BS-OA-096, BS-OA-097, BS-OA-098, BS-OA-099, BS-OA-101 and BS-OA-103 exhibit particularly remarkable effects against K562/adr cells. That is, as compared with oleanolic acid, these compounds all improve the cell inhibition rate by more than 3-fold. Further, as compared with oleanolic acid, the inventive BS-OA-096, BS-OA-097, BS-OA-098, BS-OA-099 and BS-OA-101 improve the cell inhibition rate of NB4 cells by more than 5-fold; BS-OA-099 and BS-OA-101 improve the inhibition rate of Kasumi-1 cells by more than 3-fold; BS-OA-096 and BS-OA-097 improve the cell inhibition rate of H9 cells by almost 4-fold; BS-OA-097 and BS-OA-099 improve the cell inhibition rate of Jurkat cells by more than 6-fold.

TABLE 1

Determination of the inhibitory concentrations of the amidated oleanolic acid derivatives on leukemia cell growth (72 h, $IC_{50}$ value and IR value, μg/mL).

| Compounds | K562/adr | | NB4 | | Kasumi-1 | |
| --- | --- | --- | --- | --- | --- | --- |
| | $IC_{50}$ | IR | $IC_{50}$ | IR | $IC_{50}$ | IR |
| OA | >16 | 26.5% | >16 | 17.2% | >16 | 17.2% |
| BS-OA-096 | 8.53 | 81.9% | 11.16 | 100.0% | >16 | 33.6% |
| BS-OA-097 | 2.40 | 91.3% | 6.51 | 93.4% | >16 | 42.9% |
| BS-OA-098 | 7.83 | 81.9% | 8.22 | 96.3% | >16 | 35.7% |
| BS-OA-099 | 5.26 | 97.1% | 9.17 | 100.0% | 13.11 | 69.1% |
| BS-OA-100 | >16 | 38.8% | | | | |
| BS-OA-101 | 6.29 | 88.7% | 8.2 | 96.1% | 15.42 | 53.8% |
| BS-OA-102 | >16 | 57.0% | | | | |
| BS-OA-103 | 5.70 | 87.3% | 16 | 48.5% | >16 | 19.9% |
| BS-OA-104 | 11.03 | 73.4% | 11.03 | 70.7% | >16 | 23.4% |

| Compounds | H9 | | Jurkat | |
| --- | --- | --- | --- | --- |
| | $IC_{50}$ | IR | $IC_{50}$ | IR |
| OA | >16 | 22.8% | >16 | 9.4% |
| BS-OA-096 | 10.7 | 84.0% | 15.29 | 55.3% |
| BS-OA-097 | 6.3 | 85.3% | 14.31 | 56.6% |
| BS-OA-098 | 12.5 | 62.4% | >16 | 20.1% |
| BS-OA-099 | 14 | 59.8% | 14.52 | 63.6% |
| BS-OA-101 | 14 | 58.7% | >16 | 30.0% |
| BS-OA-103 | >16 | 34.1% | >16 | −2.5% |
| BS-OA-104 | 9.5 | 73.3% | >16 | 44.1% |

Example 3

Evaluation of the Anti-Human Multiple Myeloma Cell Activities by the Amidated Oleanolic Acid Derivatives of the Present Invention (1) Experimental Materials Multiple myeloma cell lines: RPMI8226 (multiple myeloma), purchased from Fuxiang Bio-tech Co. Ltd., Shanghai, China.

Reagents: the same as in Example 2.

Main apparatuses: a cell incubator (model: Thermo Scientific 3111) and a microplate absorbance reader (model: Bio-Rad iMark).

(2) Experimental Method

Obtaining 6000 well-growing leukemia cells and inoculating them into wells of a 96-well cell culture plate. The culture medium is the 1640 cell culture medium containing 10% fetal bovine serum. After adding the amidated oleanolic acid derivatives of different concentrations and mixing uniformly, placing the plate in a carbon dioxide cell incubator (5% $CO_2$) at 37° C. and incubated for 72 hours. Then the relative number of viable cells is determined by the MTT method. In this experiment, the cell proliferation inhibition rate in control group (not treated with any compound) is set as 0%. Based on the relative number of living cells, the half maximum inhibitory concentration for the leukemia cells at 72 hours ($IC_{50}$ value of 72 hours, μg/mL) and the inhibition rate (IR) to the tumor cell proliferation by the 16 μg/mL compound at 72 hours are calculated.

(3) Experimental Results

The experimental results are shown in table 2. Table 2 shows that the amidated oleanolic acid derivatives of the present invention can induce cell death of human myeloma cells and inhibit growth of these tumor cells. Specifically, as compared with oleanolic acid, the inventive BS-OA-096, BS-OA-097, BS-OA-098, BS-OA-099, BS-OA-101, BS-OA-103 and BS-OA-104 show improved cell inhibition rate of RPMI8226 cells by more than 44-fold.

Example 4

Evaluation of the Effect of the Amidated Oleanolic Acid Derivatives of the Present Invention on Human Solid Tumor (1) Experimental Materials Human solid tumor cell lines: Hep-2 (laryngeal carcinoma), A549 (human lung cancer), CaES-17 (esophageal cancer cell), PC-3 (prostate cancer), CNE (nasopharyngeal carcinoma cell), and SK-OV-3 (ovarian cancer cell), all of which are purchased from China Center For Type Culture Collection; RKO (human colon adenocarcinoma cell), MGC 803 (human gastric cancer cell), MG63 (osteosarcoma) and U87 MG (malignant glioma cell), all of which are purchased from Fuxiang Bio-tech Co. Ltd., Shanghai, China; PANC-1 (pancreatic cancer), Hep G2 (human liver cancer cell), Becap37 (human breast cancer cell), and Hela (human cervical cancer cell), all of which are donated by Cancer Research Institute of Zhejiang University, China.

Reagents: the same as in Example 2.

Main apparatuses: a cell incubator (model: Thermo Scientific 3111) and a microplate absorbance reader (model: Bio-Rad iMark).

(2) Experimental Method

Obtaining 4000 well-growing human solid tumor cells and inoculating them into wells of a 96-well cell culture plate. The culture medium is DMEM High Glucose cell culture medium containing 10% fetal bovine serum. The plate is placed in a carbon dioxide cell incubator (5% $CO_2$) at 37° C. for 24 hours for incubation. After being added with the amidated oleanolic acid derivatives of different concentrations and mixed uniformly, the plate is placed in a carbon dioxide cell incubator (5% $CO_2$) at 37° C. for 72 hours for incubation. Then the relative number of the living cells is determined by the MTT method. In this experiment, the cell proliferation inhibition rate in control group (not treated with any compound) is set as 0%. Based on the relative number of living cells, the half maximum inhibitory concentration for the leukemia cells at 72 hours ($IC_{50}$ value of 72 hours, μg/mL) and the inhibition rate (IR) of tumor cell proliferation by the 16 μg/mL compound at 72 hours are calculated.

(3) the Experimental Results are Shown in Table 2.

Table 2 shows that the amidated oleanolic acid derivatives of the present invention can induce cell death of human solid tumor and inhibit the growth of these tumor cells. Specifically, as compared with oleanolic acid per se, the inventive amidated oleanolic acid derivatives BS-OA-096 improves the inhibition rate of PANC-1, Hela, CNE, and MGC803 cells by almost 7-fold, 4-fold, 2-fold and 3-fold, respectively, and improves the cell inhibition rate of RKO, MG63, SKOV-3 cells by more than 4-fold, 3-fold, and 12-fold, respectively; BS-OA-097 improves the cell inhibition rate of PC-3 cells by almost 2-fold and improves the cell inhibition rate of MG63 cells by more than 3-fold; BS-OA-099 improves the cell inhibition rate of RKO and A549 cells both by more than 4-fold, improves the cell inhibition rate of U87 MG and CaES-17 cells both by more than 2-fold, and improves the cell inhibition rate of Hep-2 cells by more than 3-fold.

TABLE 2

Determination of the inhibitory concentrations on multiple myeloma and human solid tumor cell growth (72 h, $IC_{50}$ value and IR value).

| Compounds | RPMI8226 | | A549 | | PANC-1 | |
|---|---|---|---|---|---|---|
| | $IC_{50}$ | IR | $IC_{50}$ | IR | $IC_{50}$ | IR |
| OA | >16 | 2.2% | >16 | 5.0% | >16 | 8.5% |
| BS-OA-096 | 9.2 | 96.9% | >16 | 18.7% | 14.67 | 59.1% |
| BS-OA-097 | 3.51 | 95.3% | >16 | 38.1% | >16 | 38.8% |
| BS-OA-098 | 6.44 | 97.6% | >16 | 24.3% | >16 | 34.7% |
| BS-OA-099 | 5.79 | 98.9% | 15 | 75.0% | >16 | 34.3% |
| BS-OA-100 | | | >16 | 15.6% | | |
| BS-OA-101 | 6.49 | 97.5% | >16 | 37.6% | >16 | 20.6% |
| BS-OA-102 | | | >16 | 13.7% | | |
| BS-OA-103 | 9.63 | 90.2% | >16 | 29.8% | >16 | 33.7% |
| BS-OA-104 | 6.63 | 95.9% | 15.63 | 51.2% | >16 | 16.9% |

| Compounds | Becap37 | | MG 63 | | Hep G2 | | RKO | |
|---|---|---|---|---|---|---|---|---|
| | $IC_{50}$ | IR | $IC_{50}$ | IR | $IC_{50}$ | IR | $IC_{50}$ | IR |
| OA | >16 | 23.4% | >16 | 29.2% | >16 | −18.5% | >16 | 14.3% |
| BS-OA-096 | >16 | 39.3% | 13.77 | 78.1% | 18.48 | 40.1% | 14.73 | 59.4% |
| BS-OA-097 | >16 | 41.3% | 13.16 | 78.6% | >16 | 35.1% | >16 | 29.0% |
| BS-OA-098 | >16 | 28.6% | >16 | 20.9% | >16 | 28.4% | >16 | 27.0% |
| BS-OA-099 | >16 | 35.1% | 15.11 | 58.9% | >16 | 25.3% | 14.3 | 63.1% |
| BS-OA-101 | >16 | 18.1% | >16 | 17.3% | >16 | 16.1% | >16 | 22.5% |
| BS-OA-103 | >16 | 4.6% | >16 | −25.4% | >16 | 8.0% | >16 | −11.7% |
| BS-OA-104 | >16 | 32.8% | >16 | 18.0% | >16 | 29.3% | >16 | 22.1% |

| Compounds | U87 MG | | Hela | | CaES-17 | | CNE | |
|---|---|---|---|---|---|---|---|---|
| | $IC_{50}$ | IR | $IC_{50}$ | IR | $IC_{50}$ | IR | $IC_{50}$ | IR |
| OA | >16 | 21.8% | >16 | 22.9% | >16 | 27.4% | >16 | 33.9% |
| BS-OA-096 | >16 | 38.5% | 9.43 | 88.9% | >16 | 39.8% | 14.02 | 63.9% |
| BS-OA-097 | >16 | 37.4% | 11.92 | 64.4% | 18.91 | 45.7% | >16 | 40.0% |
| BS-OA-098 | >16 | 29.8% | 14.17 | 63.1% | >16 | 39.9% | >16 | 35.8% |
| BS-OA-099 | 16 | 47.9% | 12.59 | 72.9% | 12.42 | 66.6% | >16 | 42.4% |
| BS-OA-101 | >16 | 36.4% | 15.84 | 57.0% | >16 | 25.8% | >16 | 36.2% |
| BS-OA-103 | >16 | 3.7% | >16 | 38.4% | >16 | −5.9% | >16 | 26.0% |
| BS-OA-104 | >16 | 40.1% | 16 | 55.0% | >16 | 27.7% | >16 | 35.5% |

| Compounds | Hep-2 | | MGC803 | | PC-3 | | SK-OV-3 | |
|---|---|---|---|---|---|---|---|---|
| | $IC_{50}$ | IR | $IC_{50}$ | IR | $IC_{50}$ | IR | $IC_{50}$ | IR |
| OA | >16 | 9.8% | >16 | 19.7% | >16 | 29.1% | >16 | 8.3% |
| BS-OA-096 | >16 | 20.6% | 13.56 | 70.0% | 18.28 | 48.1% | 10.09 | 97.0% |
| BS-OA-097 | >16 | 28.5% | 14.37 | 56.1% | 13.05 | 56.6% | 7.63 | 68.9% |
| BS-OA-098 | >16 | 19.6% | 16 | 46.3% | 17.4 | 45.1% | 14.64 | 53.5% |
| BS-OA-099 | >16 | 37.3% | 16 | 50.0% | 19.51 | 47.2% | >16 | 43.2% |
| BS-OA-101 | >16 | 7.5% | >16 | 33.2% | 19.89 | 45.7% | >16 | 39.7% |
| BS-OA-103 | >16 | 10.6% | >16 | 7.0% | >16 | 24.5% | >16 | 17.2% |
| BS-OA-104 | >16 | 20.0% | 14.47 | 55.7% | 17.67 | 47.5% | 11.91 | 54.5% |

The invention claimed is:

1. An amidated oleanolic acid derivative of formula (I), or a pharmaceutically acceptable salt thereof,

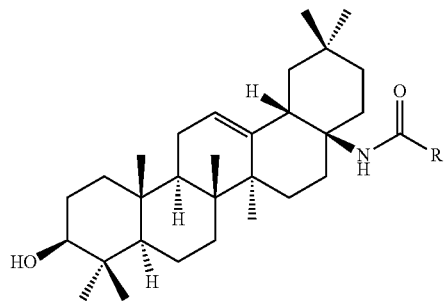

wherein R is selected from the group consisting of H, optionally substituted $C_3$-$C_7$ cycloalkyl or cycloalkenyl, optionally substituted aryl, optionally substituted heterocyclyl or heteroaryl, optionally substituted aryl-vinyl, and optionally substituted heteroaryl-vinyl, each of which is optionally substituted with a substituent selected from the group consisting of halogen, nitro, cyano, amino, hydroxyl, thiol, carboxyl, $C_1$-$C_6$ alkyl, $C_1$-$C_6$ alkylamino, $C_1$-$C_6$ alkoxy, and $C_1$-$C_6$ alkylthio.

2. The amidated oleanolic acid derivative or a pharmaceutically acceptable salt thereof according to claim 1, wherein R is selected from the group consisting of aryl, heteroaryl, cycloalkyl, heterocyclyl, aryl-vinyl, and heteroaryl-vinyl, each of which is optionally substituted by halogen, $C_1$-$C_6$ alkyl or $C_1$-$C_6$ alkoxy.

3. The amidated oleanolic acid derivative or a pharmaceutically acceptable salt thereof according to claim 1, wherein the aryl is phenyl.

4. The amidated oleanolic acid derivative or a pharmaceutically acceptable salt thereof according to claim 1, wherein the heteroaryl is furyl, thienyl, pyrrolyl, or pyridyl.

5. The amidated oleanolic acid derivative or a pharmaceutically acceptable salt thereof according to claim 1, wherein the cycloalkyl is cyclopropyl, cyclopentyl or cyclohexyl.

6. The amidated oleanolic acid derivative or a pharmaceutically acceptable salt thereof according to claim 1, wherein the heterocyclyl is tetrahydrofuryl, tetrahydrothienyl, piperidyl, piperazinyl or morpholinyl.

7. The amidated oleanolic acid derivative or a pharmaceutically acceptable salt thereof according to claim 1, wherein R is selected from optionally substituted heteroaryl-vinyl.

8. The amidated oleanolic acid derivative or a pharmaceutically acceptable salt thereof according to claim 1, which is selected from the group consisting of the following compounds:

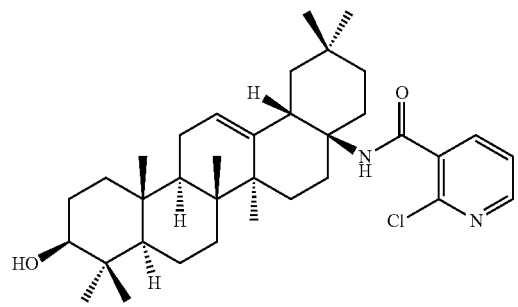

BS-OA-096

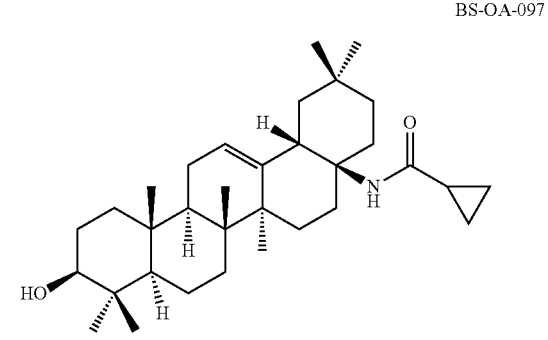

BS-OA-097

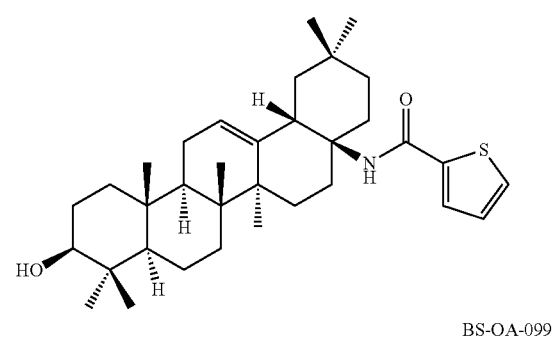

BS-OA-098

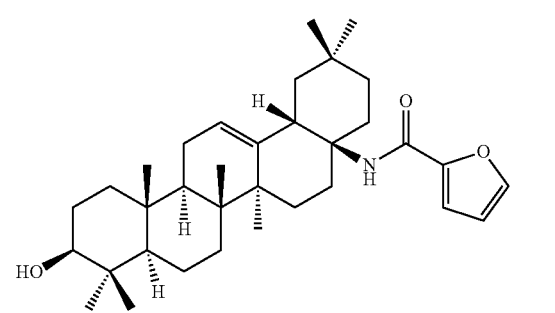

BS-OA-099

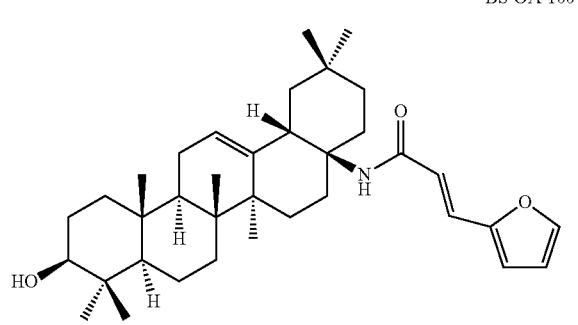

BS-OA-100

-continued

BS-OA-101

BS-OA-102

BS-OA-103

BS-OA-104

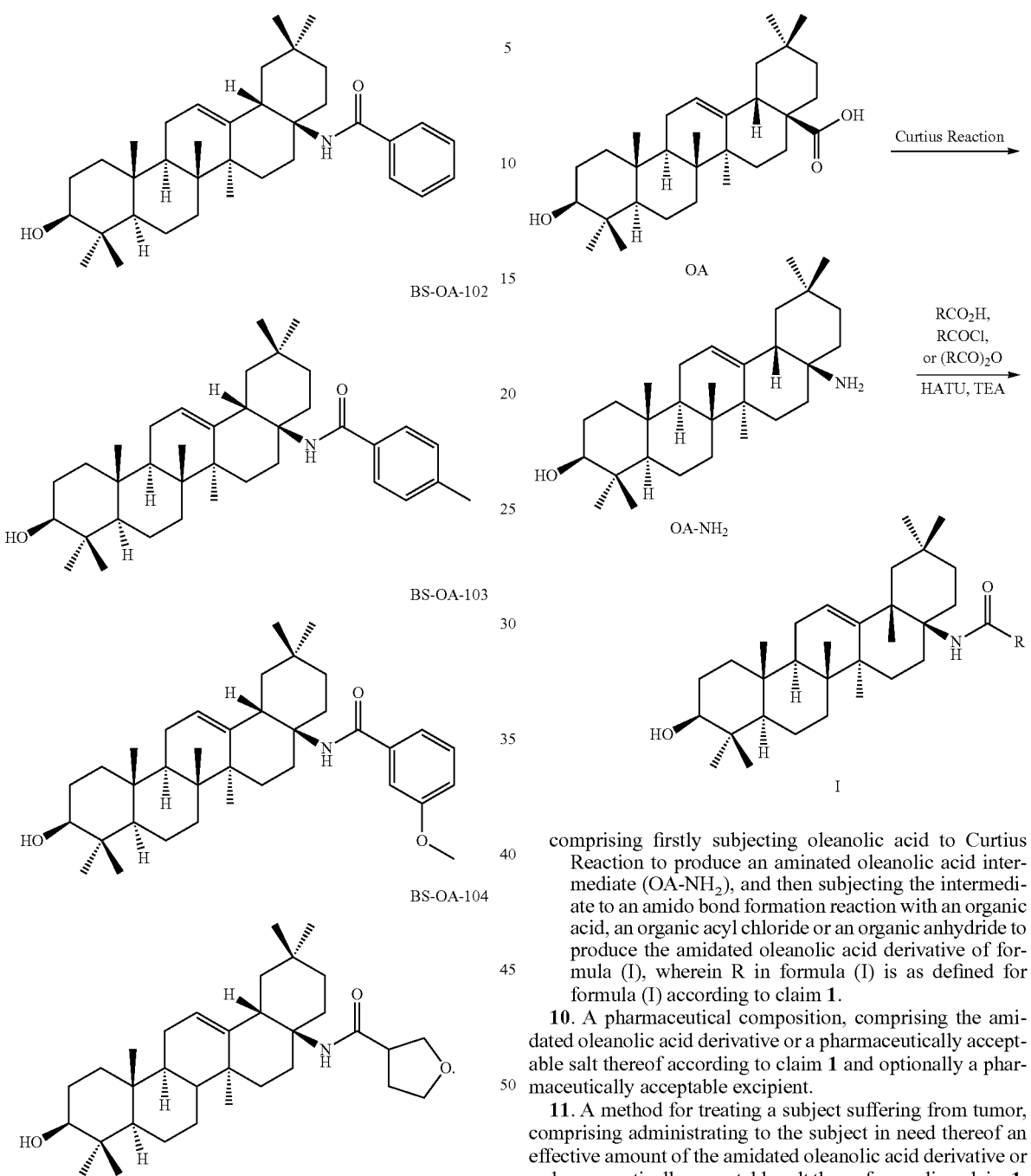

9. A process for preparing the compound of formula (I), comprising firstly subjecting oleanolic acid to Curtius Reaction to produce an aminated oleanolic acid intermediate (OA-NH$_2$), and then subjecting the intermediate to an amido bond formation reaction with an organic acid, an organic acyl chloride or an organic anhydride to produce the amidated oleanolic acid derivative of formula (I), wherein R in formula (I) is as defined for formula (I) according to claim 1.

10. A pharmaceutical composition, comprising the amidated oleanolic acid derivative or a pharmaceutically acceptable salt thereof according to claim 1 and optionally a pharmaceutically acceptable excipient.

11. A method for treating a subject suffering from tumor, comprising administrating to the subject in need thereof an effective amount of the amidated oleanolic acid derivative or a pharmaceutically acceptable salt thereof according claim 1.

\* \* \* \* \*